United States Patent [19]

Grätzel et al.

[11] Patent Number: 5,378,628
[45] Date of Patent: Jan. 3, 1995

[54] SENSOR FOR MEASURING THE AMOUNT OF A COMPONENT IN SOLUTION

[75] Inventors: Michael Grätzel, St-Sulpice; David Fraser, Vevey; Shaik M. Zakeeruddin, Renens; Jean-Paul Randin, Cortaillod; Erik J. Frenkel, Neuchâtel, all of Switzerland

[73] Assignee: Asulab, S.A., Bienne, Switzerland

[21] Appl. No.: 938,219

[22] PCT Filed: Feb. 19, 1992

[86] PCT No.: PCT/CH92/00034

§ 371 Date: Oct. 19, 1992

§ 102(e) Date: Oct. 19, 1992

[87] PCT Pub. No.: WO92/14836

PCT Pub. Date: Sep. 3, 1992

[30] Foreign Application Priority Data

Feb. 21, 1991 [FR] France .................. 91 02200

[51] Int. Cl.[6] .............. G01N 27/26; G01N 27/327
[52] U.S. Cl. ................... 435/288; 204/153.12; 204/403; 422/82.01; 435/817
[58] Field of Search ........ 435/4, 25, 288, 817; 436/95; 422/82.01; 204/403, 153.12; 128/635

[56] References Cited

U.S. PATENT DOCUMENTS

| | | | |
|---|---|---|---|
| 4,526,661 | 7/1985 | Steckhan et al. | 204/73 R |
| 4,545,382 | 10/1985 | Higgins et al. | 128/635 |
| 4,619,754 | 10/1986 | Niki et al. | 204/403 X |
| 4,684,537 | 8/1987 | Graetzel et al. | 427/554 |
| 4,970,145 | 11/1990 | Bennetto et al. | 435/14 |
| 4,974,929 | 12/1990 | Curry | 128/632 X |
| 5,198,367 | 3/1993 | Aizawa et al. | 436/518 |
| 5,205,920 | 4/1993 | Oyama et al. | 204/403 |

FOREIGN PATENT DOCUMENTS

0096288 12/1983 European Pat. Off.
8505119 11/1985 WIPO.

OTHER PUBLICATIONS

Schmehl et al. "The effect of redox site concentration on the rate ... " *J. Electroanal. Chem,* vol. 152, pp. 97–109, 1983.

Ikeda et al. "Kinetics of Outer—sphere Electron transfers ... " *J. American Chemical Society,* vol. 103, pp. 7422–7425, 1981.

Fischer et al. "Intramolecular Electron Transfer Mediated by ... " *J. American Chemical Society,* vol. 98, pp. 5512–5517, 1976.

Feldman et al. "Electron Transfer kinetics at redox polymer ... " *J. Electroanal. Chem.* vol. 194, pp. 63–81, 1985.

Pishko et al. "Amperometric Glucose Microelectrodes Prepared Through ... " *Analytical Chemistry,* vol. 63, No. 20 Oct. 25, 1991 2268–2272.

"Ferrocene—Mediated Enzyme Electrode for Amperometric Determination of Glucose", Anthony E. G. Cass, et al., *Analytical Chemistry,* vol. 56, No. 4, Apr. 1984, pp. 667–671.

"Electron—transfer biosensors", J. E. Frew and H. A. O. Hill, *Phil. Trans. R. Soc.,* vol. 316 B, London (1987), pp. 95–106.

*Primary Examiner*—Robert J. Warden
*Assistant Examiner*—Robert Carpenter
*Attorney, Agent, or Firm*—Pollock, Vande Sande & Priddy

[57] ABSTRACT

A sensor for measuring the amount of a component in solution is disclosed. The sensor has a measuring electrode with at least one current collector, electrically connected to one of the electrical contacts and coated with a mixture comprising at least one oxidation-reduction enzyme specific to said component and at least one mediator transferring the electrons between said enzyme and said current collector wherein the mediator is a transition metal complex with at least one bipyridine, terpyridine or phenanthroline ligand substituted by at least one electron donor group. This sensor is particularly useful in the detection of glucose.

14 Claims, 10 Drawing Sheets

SENSOR FOR MEASURING THE AMOUNT OF A COMPONENT IN SOLUTION

TECHNICAL FIELD

The instant invention relates to a sensor for measuring the amount of a component in solution designed to be used in an amperometric device for measuring the concentration of said component in the solution. This sensor is in particular suitable for analysing glucose.

BACKGROUND OF THE INVENTION

Many patients with diabetes frequently have to measure their blood glucose level, or glycemia. If they detect a state of hyperglycemia they immediately have to take medication to regulate their glucose level. To simplify the daily life of these patients, numerous miniaturized glucose measuring devices which can be used by a layperson have appeared on the market.

The implantation of insulin pumps in diabetics has also been proposed. These insulin pumps have to be supplied with devices for measuring glucose that can also be implanted and which, as a function of the glycemia measured, supply information to the pump and possibly start it operating.

The majority of these devices for measuring glycemia use an enzyme specific to glucose—glucose oxidase (GOD).

As shown in the appended FIG. 1, GOD is a flavoprotein (obtained for example from moulds) which catalyses the oxidation of glucose, in this case for example blood glucose, into gluconolactone, with the formation of hydrogen peroxide $H_2O_2$, starting from the molecular oxygen $O_2$ present in the solution to be tested, in this case blood.

This enzyme (GOD) and oxygen have thus frequently been used in devices for measuring glucose in which the oxidation of the glucose was detected by an electrical or optical transducer.

Similarly, this enzyme (GOD) and oxygen have frequently been used in amperometric devices and their use is described in the literature.

These amperometric devices comprise on the one hand a measuring apparatus provided with at least two electrical contacts connected to an ammeter and to display means and, on the other hand, a sensor which may be disposable and which can be connected to these two electrical contacts. This sensor comprises at least two electrodes: a reference electrode and a measuring electrode. The measuring electrode comprises a metal conductor coated with an enzyme specific to the product to be detected.

The appended FIG. 2 illustrates the chemical reactions occurring on the surface of this measuring electrode. When the solution to be tested is deposited on the measuring electrode, the product to be tested (in this case glucose) reacts with the enzyme (in this case the oxidized GOD) located on the electrode to form gluconolactone while the GOD passes into the reduced state [$GOD(H_2)_{(red)}$]. This reduced GOD then reacts with oxygen $O_2$ which passes into the reduced state $H_2O_2$ and which then transfers two electrons $e^-$ towards the electrical conductor C, the potential of which is fixed and is in the region of 650 mV. The fact that it is necessary to work at elevated potentials causes additional interference problems. The oxygen thus plays the part of mediator since it permits the transfer of electrons. This transfer of electrons, which is proportional to the amount of glucose present in the solution to be tested, is then measured by the ammeter and the amount of glucose present in the solution is displayed by the display means of the measuring apparatus.

Additional research has shown that amperometric devices using non-physiological, organic, inorganic or organometallic mediators can supplant devices using oxygen as the mediator. Indeed, as shown in FIG. 2, devices using oxygen as the mediator cannot be used in solutions where the stoichiometric oxygen content is less than the concentration of the component to be measured. Otherwise, in this case, while the total amount of the component to be measured is able to react with the oxidized enzyme to form the reduced enzyme, only part of the total amount of the reduced enzyme can react with the oxygen present, in proportion to this amount of oxygen. The rest of the reduced enzyme is unable to react and the quantity of electrons transmitted to the conductor C is less than it should be.

Consequently, when this type of device is used, one is either restricted by the respective concentrations of the oxygen and the component to be measured, or compelled to use a membrane to limit the diffusion of said component. This explains why attempts have been made to produce amperometric devices using a specific mediator to replace oxygen.

Very many mediators have been proposed in the literature, such as monomeric ferrocenes (Cass, A. E. G. et al (1984), Anal. Chem. 56, 667–671; Degani, Y. and Heller, A. (1987), J. Phys. Chem. 91, 1285–1289), ferrocenes grafted onto a polymer (Foulds, N. C. and Lowe, C. R. (1988) Anal. Chem. 60, 2473–2478), charge transfer conducting salts (Albery, W. J. Bartlett, P. N. and Craston, D. H. (1985) J. Electroanal. Chem. Interfacial. Electrochem. 194, 223–235), nickel cyclamates (Taniguchi, I., Matsushita, K., Okamoto, M., Collin, J-P and Sauvage, J-P (1990) J. Electroanal. Chem. Interfacial. Electrochem. 280, 221–226) and organic components such as quinones and benzoquinones (Kulys, J. J., and Cénas, N. K. (1983) Biochim. Biophys. Acta 744, 57). Because of major work by Hill et al, for example Frew, J. E., and Hill, H. A. O. (1987) Phil. Trans. R. Soc. Lond. B316, 95–106), the family of ferrocene components has become widely established and used as mediator for GOD and other flavoproteins. As a result, a sensor currently on the market is known to use a member of the ferrocene component family as mediator.

Unfortunately, mediators currently available rarely have the requisite ideal properties, namely an electrochemical potential adapted to the selected enzyme, adequate solubility and good chemical stability to light, temperature and pH and rapid interaction with the selected enzyme.

Moreover, the oxygen that may be present in the solutions to be tested competes with some mediators according to the diagram in the appended FIG. 3. While the mediator Med present on the conductor C continues to react with some molecules of reduced GOD, it is possible that a certain amount of the oxygen $O_2$ which may be present also reacts with other molecules of reduced GOD to form $H_2O_2$, as previously shown in FIG. 2. When measurements are made with a small potential between the measuring electrode and the reference electrode, the $H_2O_2$ traps the electrons derived from the reaction between the GOD and oxygen and these electrons no longer pass towards the electrode. Since the amount of oxygen in solution can vary, the amount of trapped electrons also varies. As a result, there is no longer any proportionality between the quantity of electrons passing towards the electrode and the amount of glucose in the solution to be tested. Under this conditions, these sensors consequently do not give reliable results.

It is an object of the invention to overcome the above mentioned disadvantages.

DISCLOSURE OF THE INVENTION

The invention therefore relates to a sensor for measuring the amount of a component in solution, comprising:

at least one measuring electrode and one reference electrode, electrically insulated from one another and designed to come into contact with said solution, said electrodes comprising respectively electrical contacts adapted to be connected to a device for processing the signal supplied by said sensor, the measuring electrode comprising at least one current collector electrically connected to one of said electrical contacts and coated with a mixture comprising at least one oxidation-reduction enzyme specific to said component and at least one mediator transferring electrons between said enzyme and said current collector.

According to the invention, the mediator is selected from complexes of a transition metal with at least one bipyridine, terpyridine or phenanthroline ligand substituted by at least one electron donor group.

As a result of the features of the sensor of the invention and especially due to the new mediators used, a family of sensors is obtained having a wide range of low oxidation-reduction potentials that remain stable in air and provide a more rapid response than the other sensors of the prior art.

BRIEF DESCRIPTION OF THE DRAWINGS

The invention will be better understood from a study of the following description of preferred embodiments of the invention given as non-limiting examples, this description being given in association with the accompanying drawings, in which.

DETAILED DESCRIPTION OF THE INVENTION

Figure 1:
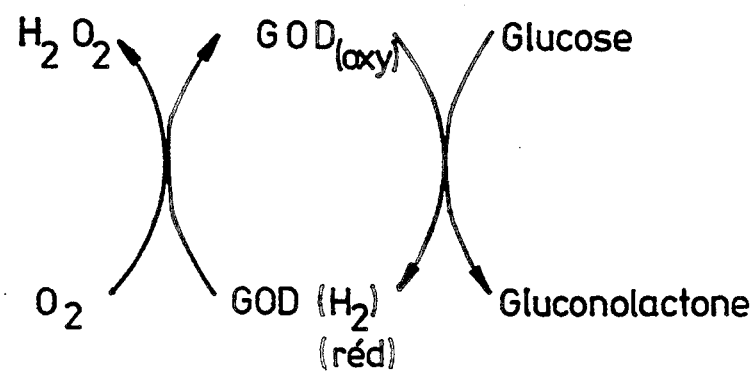
FIG. 1 illustrates the degradation of glucose in the presence of glucose oxidase GOD.
Figure 2:
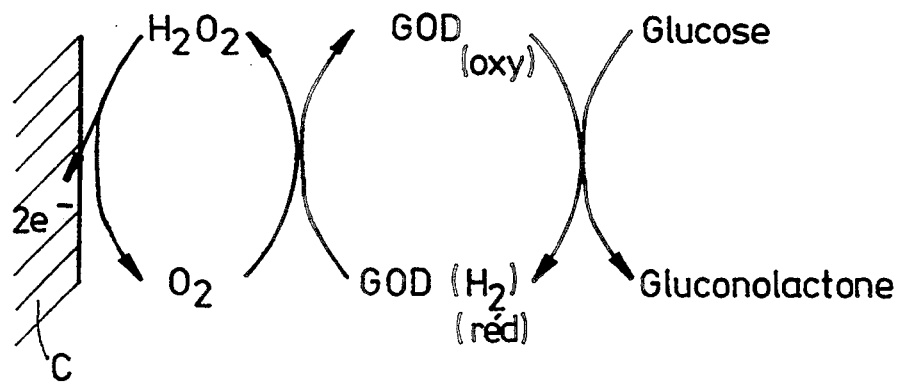
FIGS. 2 and 3 are diagrams illustrating the various chemical reactions occurring on the surface of the sensors.
Figure 3:
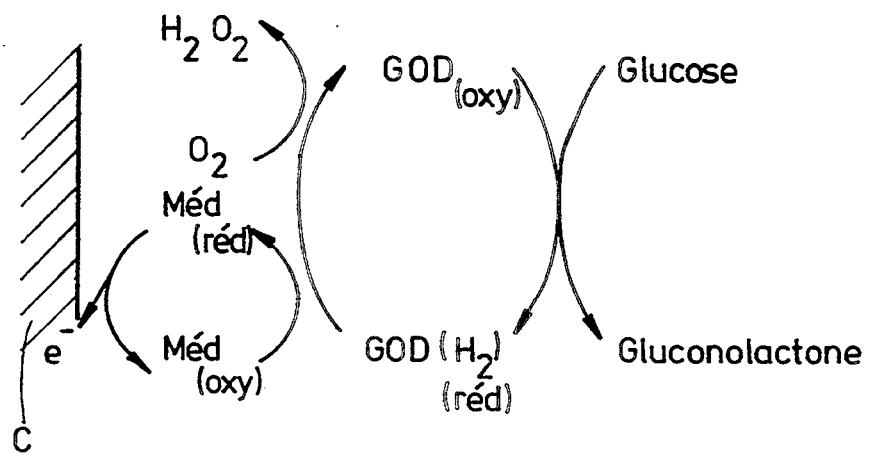
Figure 4:
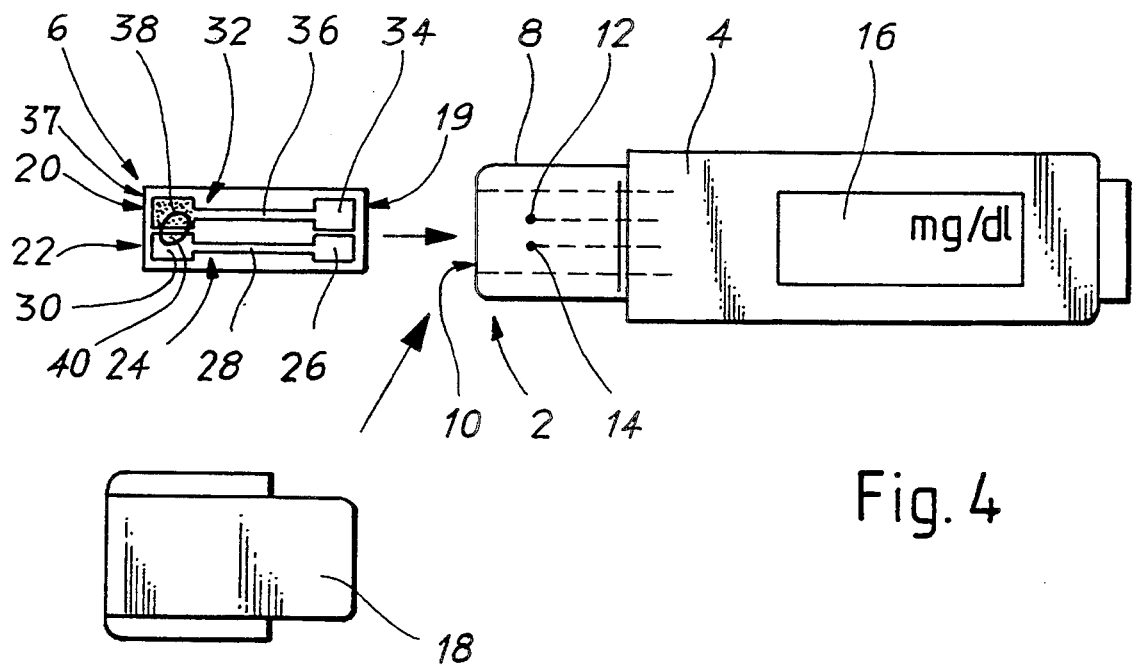
FIG. 4 is a plan view of a measuring apparatus equipped with a sensor according to the invention.

As shown in FIG. 4, the apparatus 2 for measuring the amount of a given component in a solution comprises a sensor 6 of the invention and a device 4 for processing the signal supplied by said sensor. This device 4 is known per se and is substantially shaped like a pen. The invention is of course not limited to this shape.

This pen 4 comprises at one of its extremities, bearing reference numeral 8, a cavity 10 in which are housed two first electrical contacts 12, 14 connected electrically to an ammeter (not shown). This ammeter is itself connected to a display 16 showing the concentration of the component investigated in a given solution. This concentration is displayed, for example in mg/dl or in mmol/l. The pen 4 also comprises a stopper 18 which covers its extremity 8 and protects the contacts 12, 14 when said pen is not in use.

The sensor 6 of the invention is for example shaped like an insulating rectangular wafer which can be introduced by one of its extremities bearing reference numeral 19 into the cavity 10 of the pen 4. It will be noted that this sensor 6 is disposable.

It comprises a measuring electrode 20 and a reference electrode 22 disposed, for example, longitudinally parallel on the sensor 6. The reference electrode 22 comprises a band 24 made of an electrically conducting material. This band 24 has three zones, one zone 26 termed the electrical contact provided towards the extremity 19 of said sensor, a central zone 28 termed the "conducting track" and a zone 30 provided at the other extremity of the sensor and termed the "current collector". In a somewhat similar manner, the measuring electrode 20 has a band 32 made of electrically conducting material. This band 32 also has three zones, an electrical contact 34, a conducting track 36 and a current collector 37, coated, unlike the collector 30, with a mixture 38.

On FIG. 4, this collector 37 is not clearly visible because it is hidden by the mixture 38. It will be noted that in each of these electrodes, the current collector and the current conductor could be in two parts connected electrically with one another and would not necessarily have to be in the form of a single band 24 or 32. The mixture 38 comprises at least one oxidation-reduction enzyme specific to the component to be measured and at least one mediator transferring the electrons between said enzyme and the current collector formed in the band 32.

In optional manner, the above-mentioned mixture 38 may also comprise at least one active conducting material and/or at least one additive which will be described below. In the event of the mixture 38 comprising an active conducting material, the mediator transfers the electrons between the enzyme and this active conducting material which, in turn, transfers the electrons towards the current collector.

The drop 40 of the sample of the solution to be tested is deposited across the two electrodes 20 and 22 as shown in FIG. 4. In this way, the electrical circuit composed of the ammeter, the contacts 14 and 26, the conducting track 28, the collector 30, the drop of solution 40, the mixture 38, the collector 37, the conducting track 36 and the contacts 34 and 12 is closed.

The measuring apparatus 2 which has just been described is adapted to effect measurements in vitro although it is obvious that the sensor 6 could be used in vivo in implantable measuring apparatuses. In this case, its shape or its dimensions would be adapted to this new application.

Moreover, to ensure lasting accuracy, it would be possible to add a second measuring electrode, identical to measuring electrode 20, but without the enzyme or with the denaturized enzyme.

The drop 40 of solution to be tested can be biological in nature, for example human or animal blood or urine, or a microorganism fermentation medium. It may possibly be of synthetic origin, for example a synthetic buffer containing the elements to be analyzed.

The oxidation-reduction enzyme used is an enzyme specific to the component to be measured. In accordance with the invention the enzyme used is preferably chosen from the oxidases and flavoproteins. If it is desired to make a glucose sensor, one would use glucose oxidase GOD, for example a GOD having an activity of about 250 IU, obtained using a culture of *Aspergillus niger*.

The active conducting material optionally used preferably takes the form of a powder of carbon, graphite, gold, platinum, palladium or of a conducting metal oxide, for example ruthenium oxide or in the form of a film of a conducting polymer, for example polypyrrole. The carbon preferably used is a carbon powder.

As has been previously seen, it is also possible to add an additive forming an immobilization network of the enzyme, of the mediator and/or of the active conducting material on the surface of the collector 37 of the measuring electrode 20. This additive is for example bovine serum albumin (BSA), glutaraldehyde, carbodiimide or water-soluble polymers.

The bands of electrically conducting material 24, 32 are for example made in the form of a layer of material chosen from gold, silver, platinum, palladium, carbon, graphite or an oxide of a conducting metal, such for example a ruthenium oxide. The band 24 corresponding to the reference electrode 22 is preferably silver and the band 32 corresponding to the measuring electrode 20 is platinum. More specifically, the part of the band 24 corresponding to the current collector 30 is partially chlorinated.

It has been found that a new family of complexes of a transition metal with at least one bipyridine, terpyridine or phenanthroline ligand substituted by at least one electron donor group has good mediator properties.

The electron donor group is preferably an OH group, an alkoxy group, an aryloxy group or a primary, secondary or tertiary amine group.

In the case of a glucose sensor and when the enzyme used is glucose oxidase (GOD), of the above-mentioned mediators one would preferably choose the complex tris(4,4'-dimethoxy-2,2'-bipyridine) osmium or bis(4,4'-dimethoxy-2,2'-bipyridine)- mono(4,4'-dimethyl-2,2'-bipyridine) osmium.

In the case of a glucose sensor, the mixture 38 deposited on the collector of the measuring electrode 20 comprises per 1 ml of phosphate buffer 10 mM adjusted to pH 6.8; 1 to 1000 mg of carbon powder, preferably 1 to 100 mg or better about 10 mg; 1 to 2000 IU of glucose oxidase per mg of carbon powder, preferably 10 to 300 IU or better 100 IU and 1 to 10000 $\mu$mol of mediator per mg of carbon powder, preferably 10 to 300 $\mu$mol or better 50 $\mu$mol. This mixture is deposited at the rate of 10 to 300 $\mu$l/cm$^2$ of active surface, preferably 30 to 150 $\mu$l/cm$^2$ or better 70 $\mu$l/cm$^2$.

In the finished, dried sensor, the mixture 38 is thus supposed to comprise 1 to 2000 IU of glucose oxidase per mg of carbon powder, preferably 10 to 3000 IU or better 100 IU and 1 to 10000 $\mu$mol of mediator per mg of carbon powder, preferably 10 to 300 $\mu$mol or better 50 $\mu$mol.

The sensor of the invention, supplied with the above-mentioned mediators presents a certain number of properties that vary as a function of the ligands used and of the substitutions effected on these ligands.

Several experiments have been conducted which prove the performance and efficacy of these new mediators and which give optimization conditions of the various elements constituting the measuring electrode. These experiments are described below.

EXPERIMENT 1

Measurements of various mediators using cyclic voltametry.

a) measurements made using the complex tris(4,4'-dimethoxy-2,2'-bipyridine) osmium.

Figure 5:
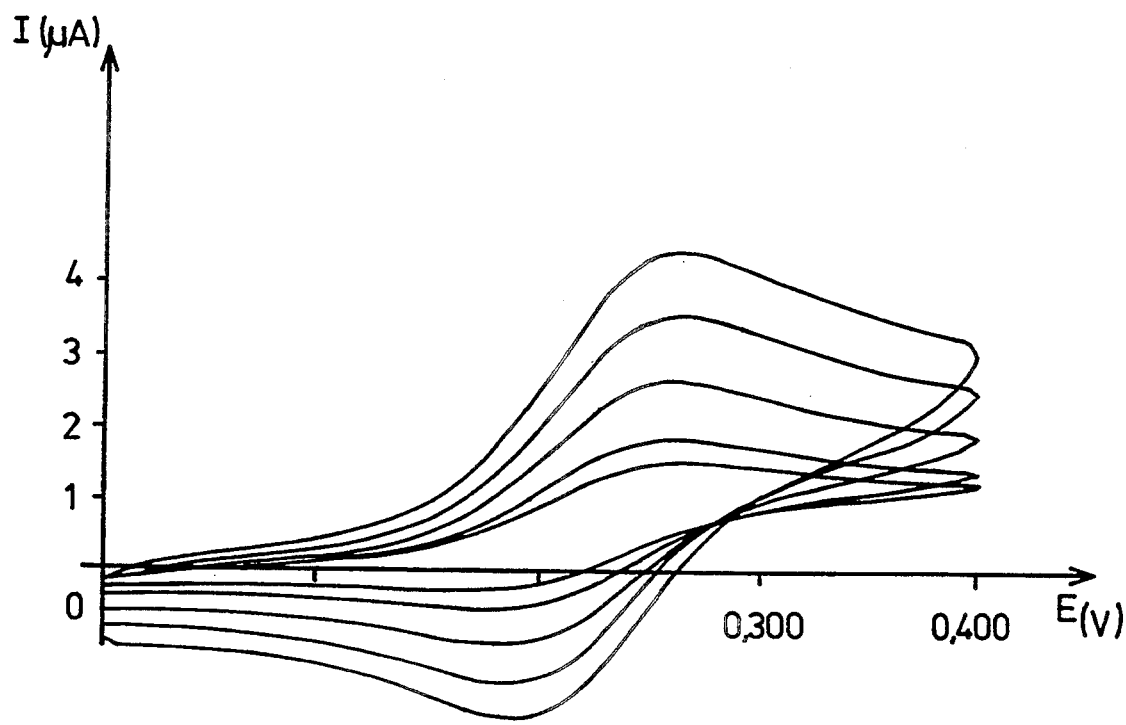
FIG. 5 shows the cyclic voltametric curves of the complex tris(4,4'-dimethoxy-2,2'-bipyridine) osmium in the absence of GOD and of glucose at different scanning speeds.
Figure 6:
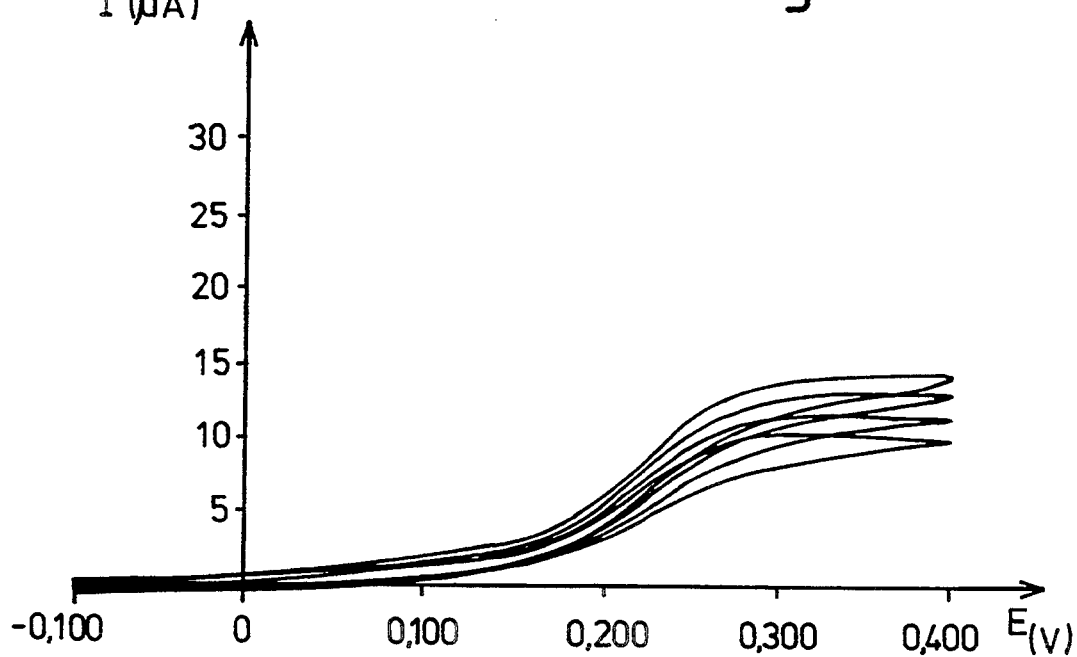
FIG. 6 shows substantially the same curves as FIG. 5, but in the presence of GOD and glucose.

The above-mentioned complex was tested using cyclic voltametry in direct current in order to determine on the one hand its normal oxidation-reduction potential E° and, on the other hand, the k rate constant. This constant k corresponds to the electron transfer reaction starting from the GOD towards the mediator. Cyclic voltametry consists of arranging a working electrode, a counter-electrode and a reference electrode in the solution to be analysed, in then scanning the potential of the working electrode at constant speed and between two terminals, and in measuring the intensity of the current obtained. The curves of FIGS. 5 and 6 show the results obtained using this method. These experiments were conducted with a vitreous carbon working electrode, a mercurous chloride reference electrode, a platinum counter-electrode and an electrochemical cell of 5 to 20 ml. The measurements were taken in a phosphate buffer PBS (NaCl 100 mM, NaH$_2$PO$_4$ 10 mM, adjusted to pH 7.4; EDTA (ethylenediamintetra-acetic acid) 0.01 mM; PMSF (phenylmethylsulfonate fluoride) 0.01 mM and with the above-mentioned complex in a concentrations of $5.10^{-4}$M. Various scanning speeds of the potentials were used: 5, 10, 25, 50 and 100 mV.s$^{-1}$. The curves of FIG. 5 and a value for E° of 225 mV are obtained. Addition of a saturated glucose solution has no effect on the curves of FIG. 5, which is normal since no glucose oxidase (GOD) is present.

In contrast, addition of GOD (in an amount greater than $5.10^{-8}$M, preferably $4.10^{-6}$M) gives rise to the curves of FIG. 6, presenting a characteristic shape so-called "catalytic wave". In this FIG. 6 the potential scanning speed used was 10, 25, 50 and 100 mV.s$^{-1}$.

One obtains a first reaction:

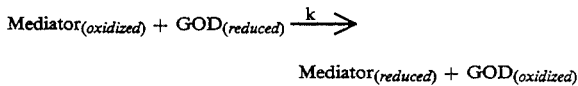

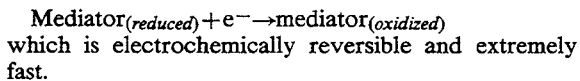

which is irreversible, (with a constant k), and a second reaction
Mediator$_{(reduced)}$ + e$^-$ → mediator$_{(oxidized)}$
which is electrochemically reversible and extremely fast.

The mediator effects an electrochemically reversible transfer of an electron towards the previously described current collectors.

During the first reaction it is possible to measure the second order constant k. For the complex studied here $k = 2.5.10^6 \pm 0.5 M^{-1}.s^{-1}$.

b) measurements made using other complexes.

Experiments similar to those which have just been described were conducted for other complexes. Table 1 gives the values of the k rate constant found and of the normal oxidation-reduction potentials E° in mV in relation to a mercurous chloride (SCE) reference electrode.

the literature. Moreover, this range of potentials is also much wider than those obtained with the ferrocene family. This is due to the large number of substituents which can be used and to the larger number of combinations of possible substitutions.

The second order constant $k_f$ corresponding to the rate constant of the oxidation-reduction reaction between the enzyme and the mediator of the invention is much faster than with the other hitherto known mediators and is faster than with oxygen. Oxygen only has a constant k of $1.5.10^6 M^{-1}.s^{-1}$. This limits the above-mentioned problems of competition between oxygen and the mediator during the electron transfer reaction from the GOD. Moreover, because the other competing reactions occur much more slowly, they do not influence the result of the measuring apparatus.

The mediators selected for the glucose sensors were consequently the complexes 1 and 2 which have at the same time a high k constant and a low normal oxidation-reduction potential E° nonetheless greater than −300 mV, which corresponds to the normal potential of the group FAD/FADH$_2$ of GOD.

EXPERIMENT 2

Optimization of various components of the mixture of the measuring electrode.

After having determined the two mediators which seem most favourable for a glucose sensor, an attempt was then made to try to determine the optimum amounts of respectively the various constituents of the mixture deposited on the collector of the measuring electrode.

This was done by preparing a mixture 38 comprising one of the two above-mentioned preferred complexes, of carbon powder, immobilized glucose oxidase and, as additive, bovine serum albumin and glutaraldehyde and then depositing on the current collector part 37 of the electrically conducting band 36 an amount of 70 μl of this mixture per cm$^2$ so as to constitute a measuring electrode 20. Various types of measuring electrodes were then made by gradually varying one of the components of the mixture and maintaining the others constant.

The various sensors prepared in this manner were used for potentiostatic measurements at a potential of

TABLE 1

| | Complex | | E° (mV$_{/SCE}$) | k(M$^{-1}$·s$^{-1}$) |
|---|---|---|---|---|
| 1 | Tris(4,4'-dimethoxy-2,2'-bipyridine) osmium complex | | 225 | $2.5.10^6$ |
| 2 | Bis(4,4'-dimethoxy-2,2'-bipyridine)mono(4,4'-dimethyl-2,2'-bipyridine) osmium complex | | 340 | $2.10^6$ |
| 3 | Bis(4,4'-dimethyl-2,2'-bipyridine)mono(4,4'-dimethoxy-2,2'-bipyridine) osmium complex | | 390 | N.D. |
| 4 | Mono(4,4'-dimethoxy-2,2'-bipyridine)mono(4,4'-dihydroxy-2,2'-bipyridine)mono(4,4'-dimethyl-2,2'-bipyridine) osmium complex | pH < 4.5<br>pH > 4.5 | 340<br>190 | N.D.<br>$2.10^5$ |
| 5 | Tris(4,4'-dimethyl-2,2'-bipyridine) osmium complex | | 425 | $1.5.10^6$ |
| 6 | Tris(4,4'-dihydroxy-2,2'-bipyridine) osmium complex | | −1000 | ≃0 |
| 7 | Tris(4,4'-diamino-2,2'-bipyridine) ruthenium complex | | 170 | $1.6.10^6$ |
| 8 | Tris(4,4'-diamino-2,2'-bipyridine) iron complex | | 70 | $1.4.10^5$ |

N.D. = not determined.

It will be noted from this Table 1 that the family of mediators has a very wide range of redox potentials, varying between −1000 mV and +425 mV (in relation to a mercurous chloride SCE reference electrode). The lower limit of this range is much lower than all the redox potentials of the mediators hitherto described in 300 mV in multiple blood samples containing various amounts of glucose. The results are set out below.

a) Optimization of the amount of carbon powder.

Various different types of sensors have been made (but it was decided only to use three), by mixing into 3 ml of phosphate buffer PBS a constant amount of GOD, (36.9 mg), a constant amount of the complex bis(4,4'-dimethoxy-2,2'-bipyridine)- mono(4,4'-dimethyl-2,2'-bipyridine) osmium (3.0 mg), used as mediator, a constant amount of glutaraldehyde at 25% (25 µl), a constant amount of bovine serum albumin at 15% (290 µl) and, respectively, 25, 50 or 250 mg of carbon powder.

The phosphate buffer PBS used here and in the below-mentioned experiments is a 10 mM buffer adjusted to pH 6.8.

These three types of sensor were then tested in a physiological solution containing different amounts of glucose (between 0 and 20 mM of glucose) and the density of the current obtained after 30 seconds ($D_{30}$) was measured. The physiological solution is composed of NaCl 115 mM, KCl 25 mM, $K_2HPO_4.3H_2O$ 5 mM and $KH_2PO_4$ 0.5 mM.

Figure 7:
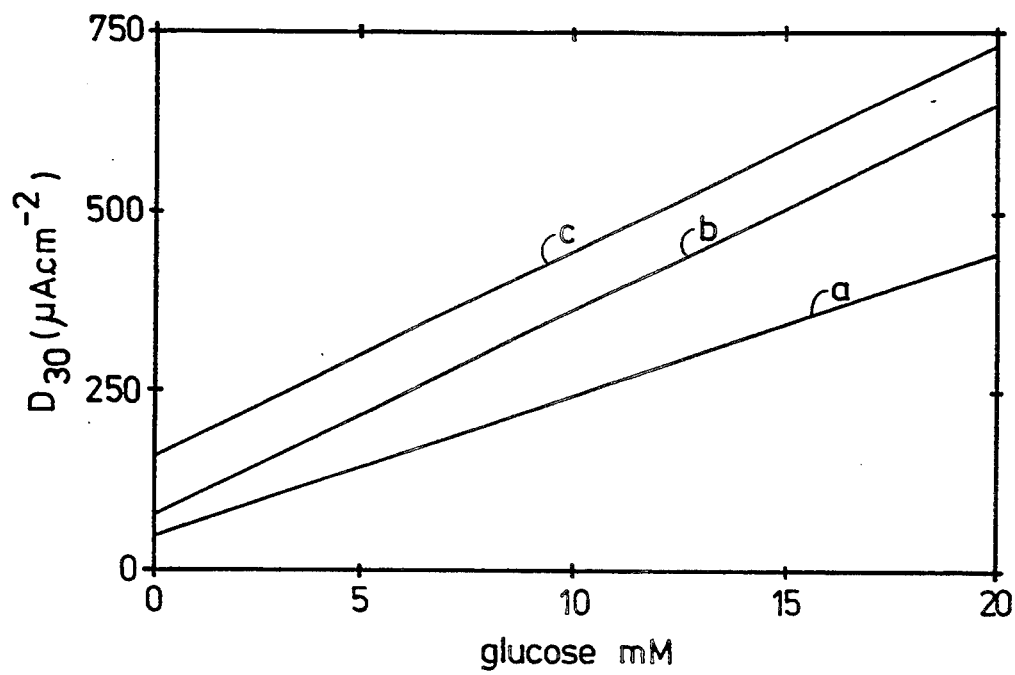
FIG. 7 shows three curves illustrating the variation in the current density obtained after 30 seconds ($D_{30}$) as a function of the glucose concentration in a physiological solution for measurements made using three types of sensor according to the invention in which the amount of carbon powder varies.

The results obtained are shown in FIG. 7 where the straight lines a, b, c correspond respectively to the results observed with the sensors containing 25, 50 and 250 mg of carbon in 3 ml of phosphate buffer PBS, or the approximate concentrations of 8, 17 and 83 mg per ml. There too, it should be noted that many more measurements were conducted, but it was decided only to show the straight lines a, b, c.

Figure 8:
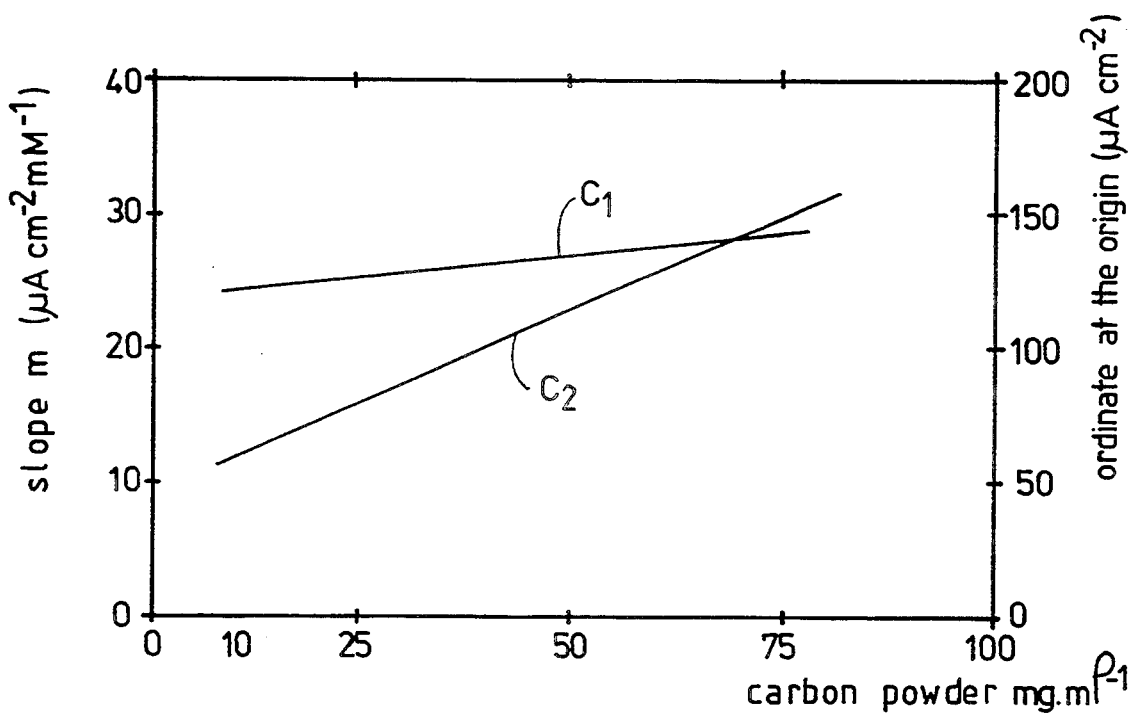
FIG. 8 shows the gradient and the ordinate at the origin of the curves of FIG. 7 as a function of the amount of carbon powder.

The gradient (m) was then calculated for all the straight lines representing the totality of the measures effected and these values were transferred to FIG. 8 (curve $C_1$) where the axis of the abscissae represents the amount of carbon in mg per ml of phosphate buffer PBS. Similarly, the ordinate at the origin of these straight lines was calculated and these values were transferred to FIG. 8 (curve 2). The ordinate at the origin corresponds to the value of the point of intersection of a straight line of FIG. 7 and of the axis of the ordinates, that is to say to the value of the residual current.

It will be noted that the curve $C_1$ is substantially horizontal between 17 and 83 mg of carbon, which signifies that between these two values the amount of carbon has little influence on the results of the sensor. Nonetheless, since a thin layer of carbon presents better mechanical and diffusional properties, preference was given to using as little carbon as possible. It will, moreover, be noted that the value of the ordinate at the origin of the straight line a (8 mg of carbon per ml) is smaller, which indicates that the smallest residual current has been reached.

It is consequently preferable to use about 10 mg of carbon per ml of phosphate buffer PBS.

b) Optimization of the amount of enzyme (GOD).

Several different types of sensors were made, (but it was decided only to show three), by mixing in 3 ml of phosphate buffer PBS a constant amount of carbon (25 mg), a constant amount (3 mg) of the same mediator as that of paragraph a) constant amounts of glutaraldehyde at 25% (25 µl) and of bovine serum albumin at 15% (290 ul) and amounts of 2175, 4375 and 8750 IU of glucose oxidase GOD respectively which gave concentrations of GOD of 87, 175 and 350 IU of glucose oxidase (GOD) per mg of carbon.

Figure 9:
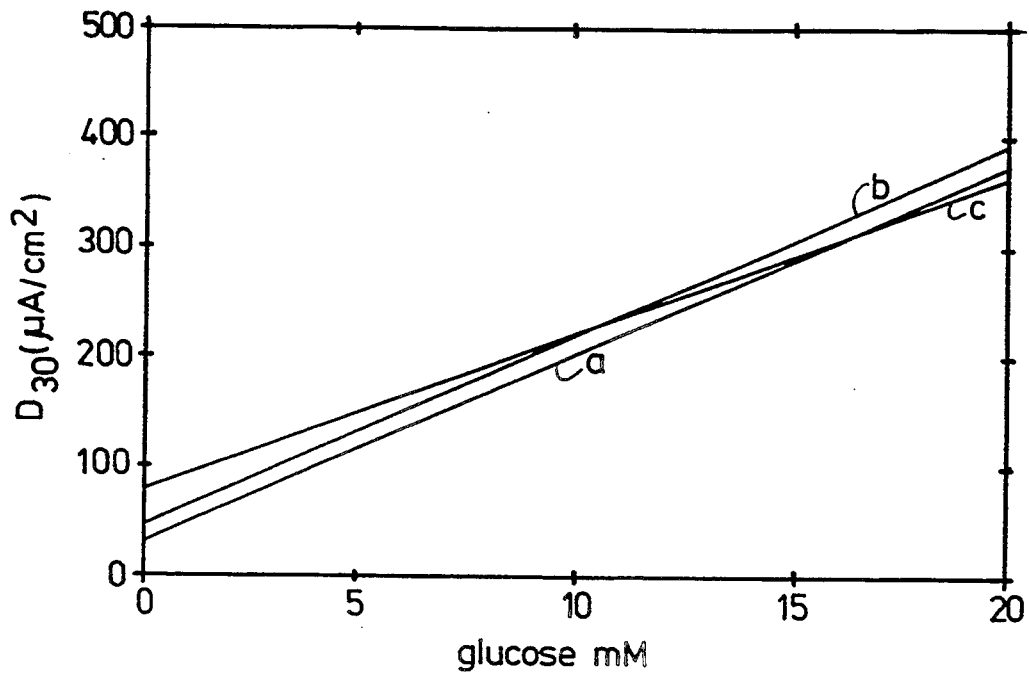
FIG. 9 shows three curves illustrating the variation in current density obtained after 30 seconds ($D_{30}$) as a function of the glucose concentration in a physiological solution for measurements conducted with three types of sensor according to the invention, in which the amount of glucose oxidase varies.
Figure 10:
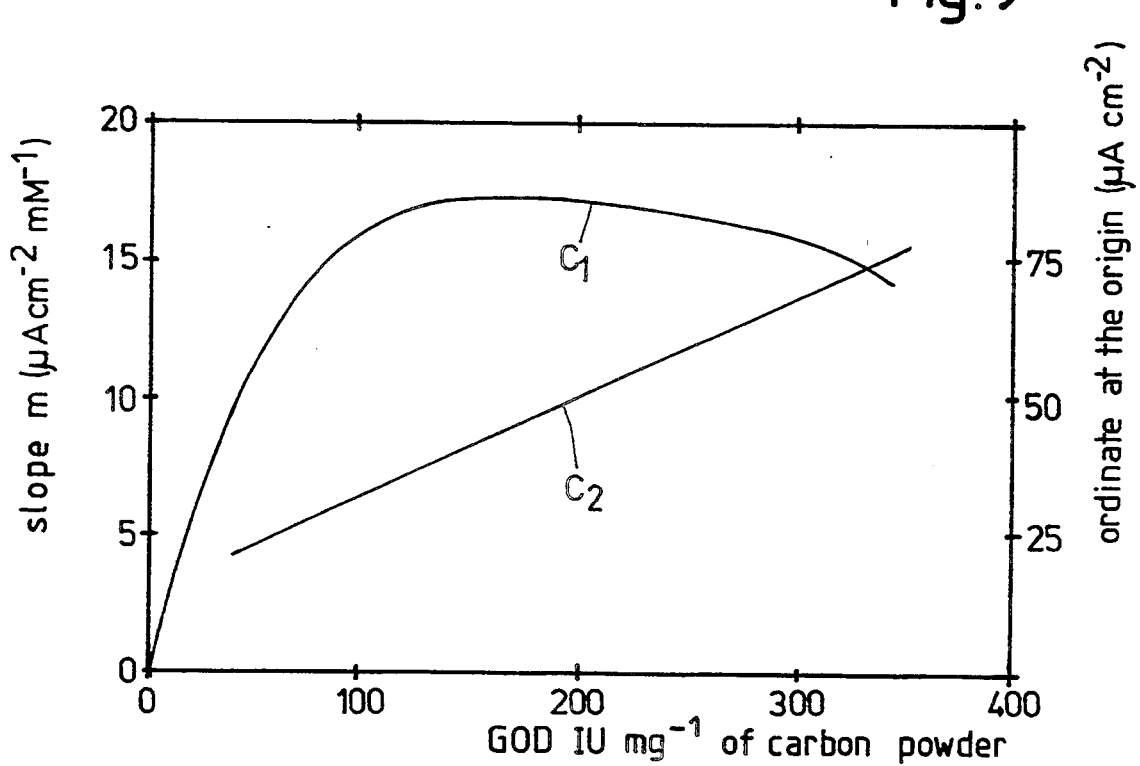
FIG. 10 shows the gradient and the ordinate at the origin of the curves of FIG. 9 as a function of the amount of glucose oxidase.

The same series of measurements and calculations were then conducted as in paragraph a). The straight lines a, b, c of the FIG. 9 correspond respectively to the results observed with sensors containing 87, 175 and 350 IU of glucose oxidase per mg of carbon powder. The curves $C_1$ and $C_2$ of FIG. 10 show the gradient (m) and the ordinate at the origin respectively. The axis of the abscissae of FIG. 10 expresses the amount of GOD in IU per mg of carbon powder.

It will be noted that between 75 and 350 IU of GOD per mg of carbon powder, the curve $C_1$ is substantially horizontal, which means that between these two values the amount of GOD has little influence on the results. Moreover, the ordinate at the origin of the line a is the smallest one which means that one has the smallest residual current.

It was consequently preferred to use about 100 IU of GOD per mg of carbon powder.

c) Optimization of the amount of mediator.

Three different types of sensor were made by mixing in 3 ml of phosphate buffer PBS a constant amount of carbon (25 mg), a constant amount of GOD (36.9 mg), constant amounts of glutaraldehyde at 25% (25 ul) and of bovine serum albumin at 15% (290 ul) and respectively 825; 1675 and 3325 µmol of the complex bis(4,4'-dimethoxy-2,2'-bipyridine)- mono(4,4'-dimethyl-2,2'-bipyridine) osmium namely mediator concentrations of 33; 67 and 133 µmol per mg of carbon powder.

Figure 11:
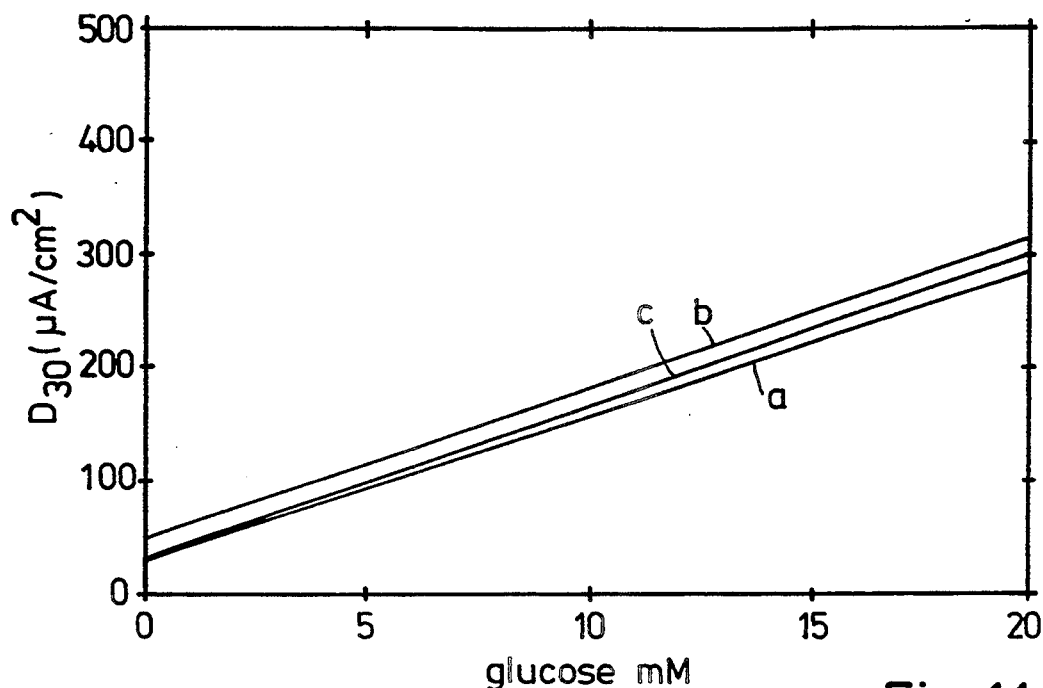
FIG. 11 shows three graphs illustrating the variation in current density obtained after 30 seconds ($D_{30}$) as a function of the glucose concentration in a physiological solution for the measurements conducted with three types of sensor according to the invention, in which the amount of mediator varies.
Figure 12:
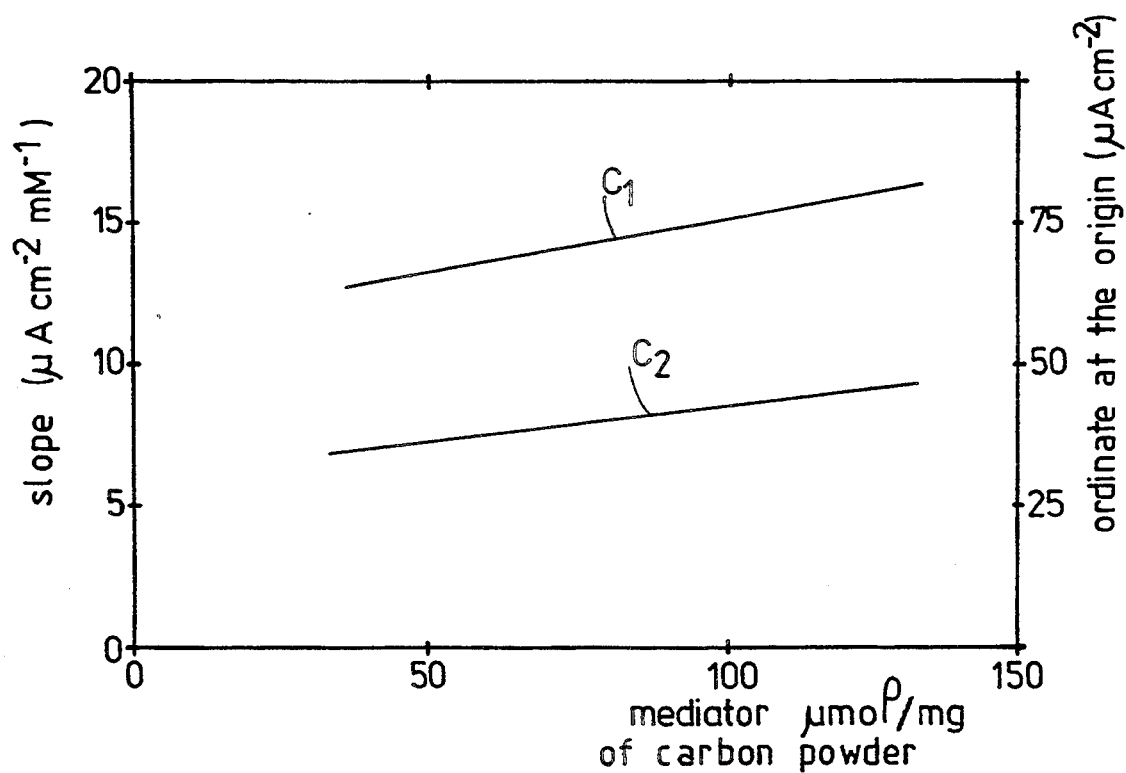
FIG. 12 shows the gradient and the ordinate at the origin of the curves of FIG. 11 as a function of the amount of mediator.

The same series of measurements and calculations were then conducted as in paragraph a). The straight lines a, b, c of FIG. 11 correspond respectively to the results observed with 33; 67 and 133 µmol of this complex per mg of carbon. The curves $C_1$ and $C_2$ of FIG. 12 represent respectively the gradient (m) and the ordinate at the origin. The axis of the abscissae of FIG. 12 represents the amount of mediator in µmol per mg of carbon powder.

It will be noted that the curves $C_1$ and $C_2$ are substantially horizontal. For mediator values lower than 50 µmol it is necessary to effect measurements at a potential higher than 300 mV. Since it is preferred to work at the lowest possible potential it is therefore preferable to use about 50 µmol of mediator per mg of carbon powder.

The optimizations effected for the complex bis(4,4'-dimethoxy-2,2'-bipyridine)mono(4,4'-dimethyl-2,2'-bipyridine) osmium are also valid for the complex tris(4,4-dimethoxy-2,2'-bipyridine) osmium.

EXPERIMENT 3

Calibration of the sensor in blood and in buffer

Figure 13:
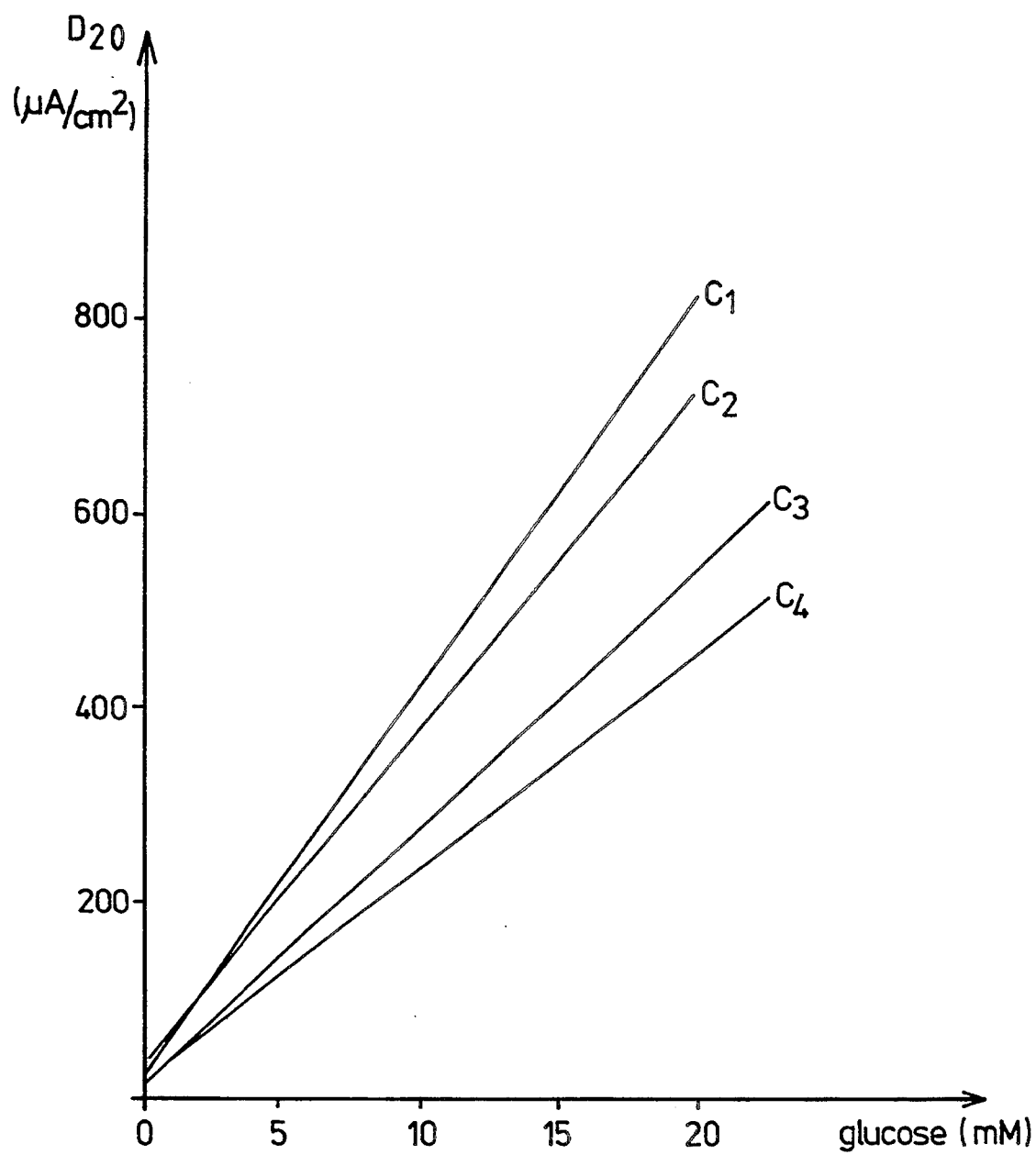
FIG. 13 shows the current density measurements obtained as a function of the glucose concentration, these measurements being effected in blood and in a phosphate buffer with the glucose sensors equipped respectively with one of the two preferred mediators of the invention.

The curves of FIG. 13 illustrate potentiostatic measurements conducted with sensors having as mediator the two preferred complexes of the invention and by varying the glucose concentration in samples of blood or of phosphate buffer PBS. Measurements were made at 300 mV and the reading of the current density $D_{20}$ was made after 20 seconds.

The curves $C_1$ and $C_3$ correspond respectively to measurements effected in phosphate buffer and in blood with a sensor using the complex tris(4,4'-dimethoxy-2,2'-bipyridine) osmium, whereas the curves $C_2$ and $C_4$ correspond respectively to measurements effected in a phosphate buffer and in blood with a sensor using the complex bis(4,4'-dimethoxy-2,2'-bipyridine)- mono(4,4'-dimethyl-2,2'-bipyridine) osmium.

As shown in FIG. 13, the various curves are linear and have a sufficiently steep gradient up to values of 20 mM of glucose. Consequently, in a patient where the physiological values of glucose can vary typically between 3 to 20 mM the sensor of the invention is reliable because a small variation in the glucose concentration corresponds to sufficient variation in the density of the current measured.

The differences observed between the measurements effected in PBS buffer and in whole blood are due to the same phenomenon as that described notably in (Fogh-Andersen, N. et al (1990), Clin. Chim. Acta 189, 33–38), for plasma and whole blood. This difference is mainly due to the volume occupied by proteins in whole blood.

EXPERIMENT 4

The influence of hematocrit on the results supplied by the sensor.

Figure 14:
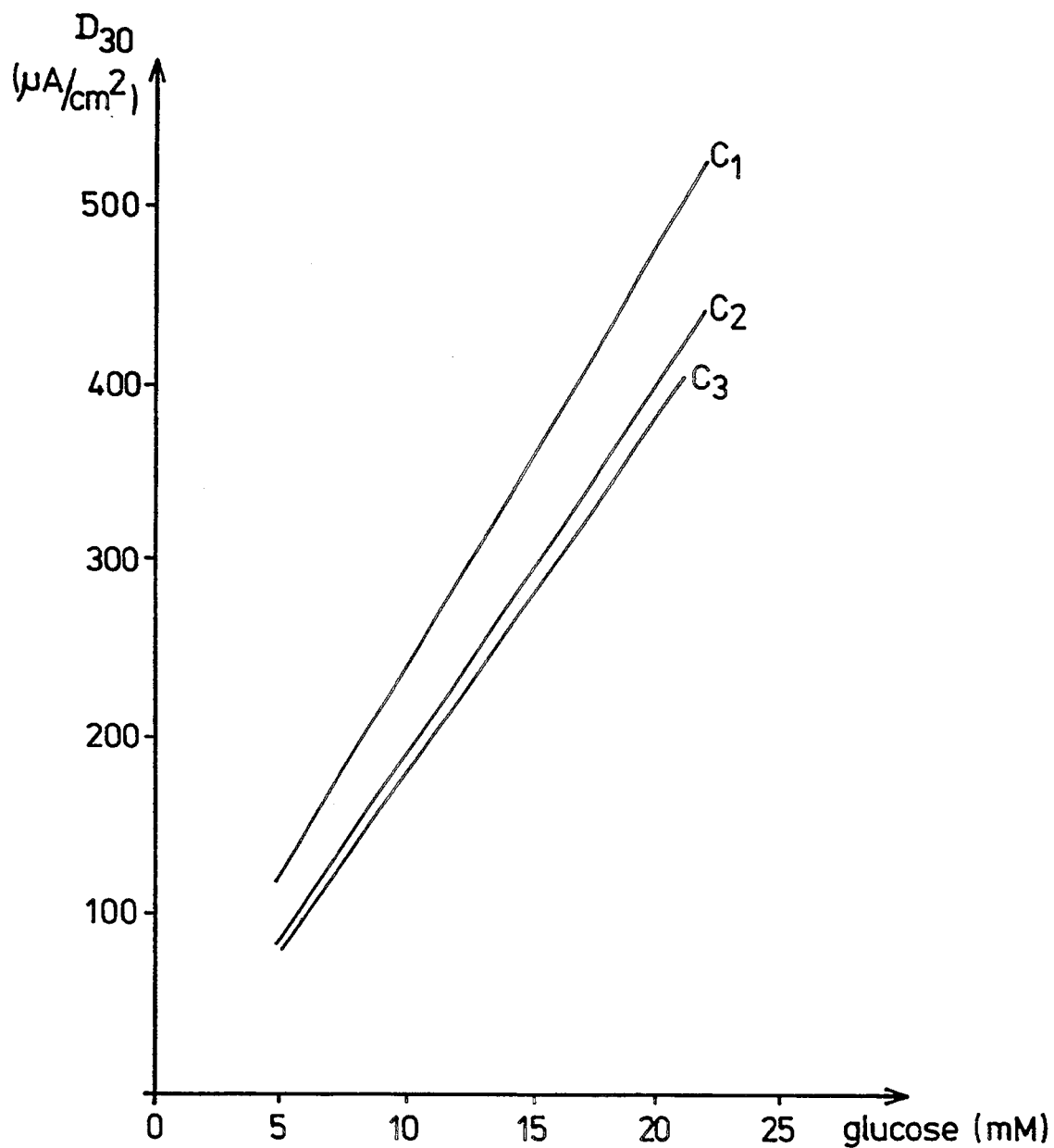
FIG. 14 shows the current density measurements obtained as a function of the glucose concentration, these measurements being carried out with the sensors of the invention in blood samples having different hematocrits.

The curves of FIG. 14 illustrate the variations in current density ($D_{30}$) obtained after 30 seconds as a function of the glucose concentration in artificially reconstituted human blood. The blood samples were prepared in the following manner. Plasma and blood cells were separated by centrifugation at 3000 revolutions per minute for 15 minutes at 4° C. The blood was then reconstituted so as to obtain various hematocrit values (0.35; 0.50 and 0.60) and known amounts of glucose were added to these samples. The glucose concentration was measured using a calibrated laboratory apparatus, for example apparatus reference 23A (supplied by Yellow Springs Instrument, Yellow Springs, Ohio). Potentiostatic measurements were conducted at 300 mV with sensors having as mediator the complex bis(4,4'-dimethoxy-2,2'-bipyridine)mono(4,4'-dimethyl-2,2'-bipyridine) osmium. The current density measurements were carried out after 30 seconds.

The curves $C_1$, $C_2$ and $C_3$ correspond respectively to samples containing 35% of cells and 65% of plasma, 50% of cells and 50% of plasma and 60% of cells and 40% of plasma.

The curve $C_2$ corresponds to a normal hematocrit. It was found that the curve $C_3$ (hematocrit 0.60) corresponding to an elevated hematocrit differs hardly at all from the curve $C_2$.

In contradistinction thereto, the curve $C_1$ (hematocrit 0.35) corresponding to the hematocrit of an anaemic patient differs from the curve $C_2$.

Consequently, the sensor of the invention gives reliable results in a patient having an elevated hematocrit but less reliable ones in all anaemic patient.

EXPERIMENT 5

The influence of pH on the activity of the mediator of the complex tris(4,4'-dimethoxy-2,2'-bipyridine) osmium and of the complex bis(4,4'-dimethoxy-2,2'-bipyridine)mono(4,4'-dimethyl-2,2'-bipyridine) osmium.

These two complexes were mixed in a PBS buffer phosphate solution in which the pH was varied and in which the normal oxidation-reduction potential E° was measured.

A stable potential E° was observed for a pH between 1 and 12. This potential E° is +225 mV for the first complex and +340 mV for the second. Since in practice the pH of human blood is about 7.4, small variations in blood pH do not affect the glycemia result given by the sensor of the invention.

EXPERIMENT 6

The influence of the presence of certain medicaments on the results supplied by the sensor.

Finally, a last series of experiments was conducted to verify whether the results supplied by this sensor could be influenced by medicaments present in the blood at the moment of measurement. In practice, a patient may well have ingested medicaments such as Asprin or vitamin C before the glycemia is measured.

The possible influence of acetylsalicylic acid, acetaminophenol and ascorbic acid on the results supplied by the sensor of the invention was therefore tested.

The experiments were conducted with a sensor using as mediator the complex tris(4,4'-dimethoxy-2,2'-bipyridine) osmium.

Potentiostatic measurements were carried out at 300 mV. Current density ($D_{30}$) was read after 30 seconds. The various curves represent the variations in current density as a function of glucose concentration, when different amounts of each of the medicaments tested are present in a sample of physiological solution.

The following results were obtained:

Acetaminophenol

Figure 15:
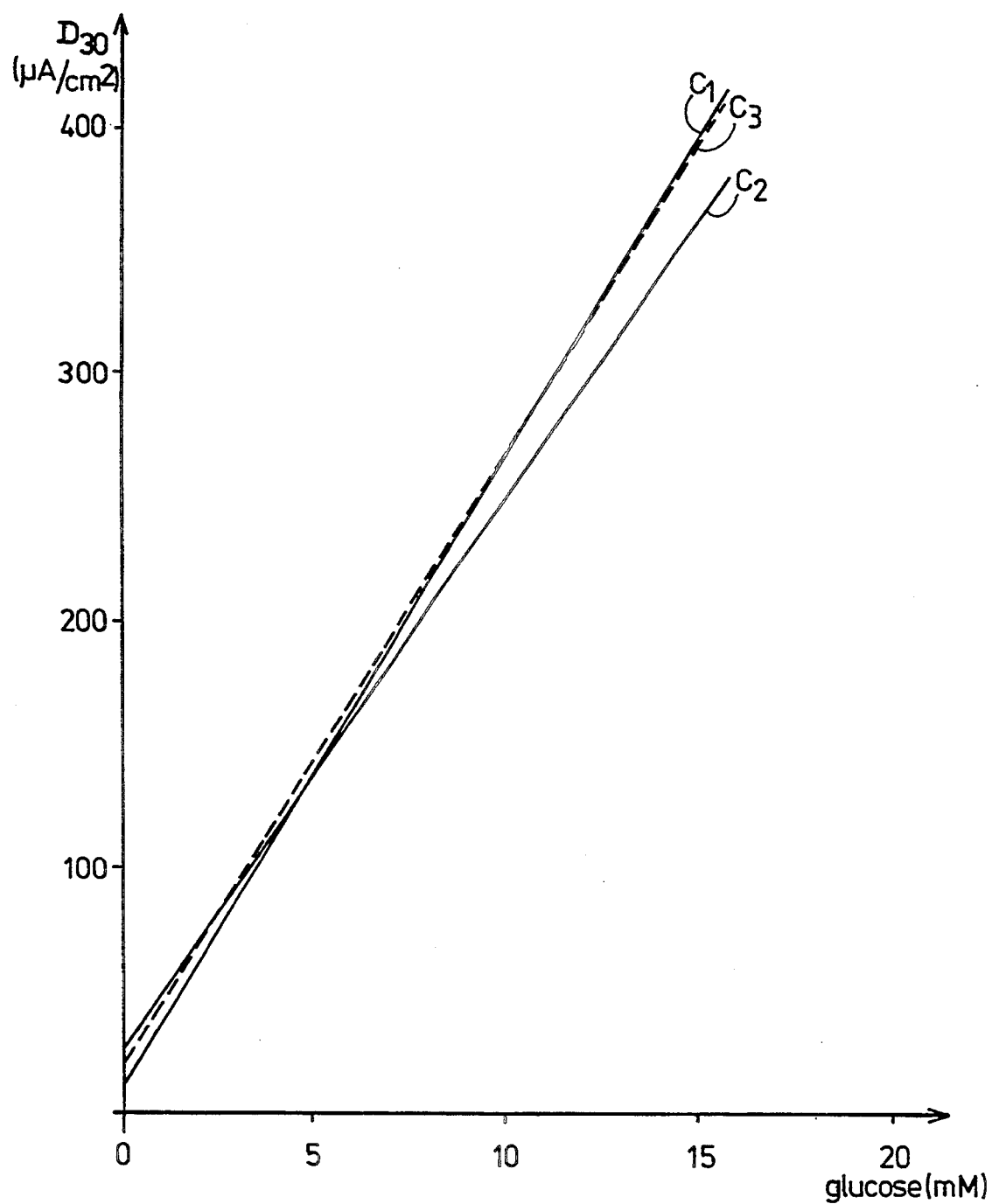
FIGS. 15 and 16 show current density measurements obtained as a function of glucose concentration, these measurements being effected using the sensors of the invention in samples of physiological solution presenting respectively various concentrations of acetaminophenol and ascorbic acid.

FIG. 15 illustrates the curves obtained. The curves $C_1$, $C_2$ (dotted line) and $C_3$ correspond respectively to concentrations of 0, 50 and 500 uM acetaminophenol.

The value of 50 um corresponds to that encountered in a patient absorbing a normal dosage of acetaminophenol whereas the value 500 um corresponds to an excess. It will be noted that between 4 and 10 mM of glucose (corresponding substantially to the physiological values), the presence of this mediator has hardly any influence on the results supplied by this sensor because all the curves are substantially superimposed.

Ascorbic acid

Figure 16:
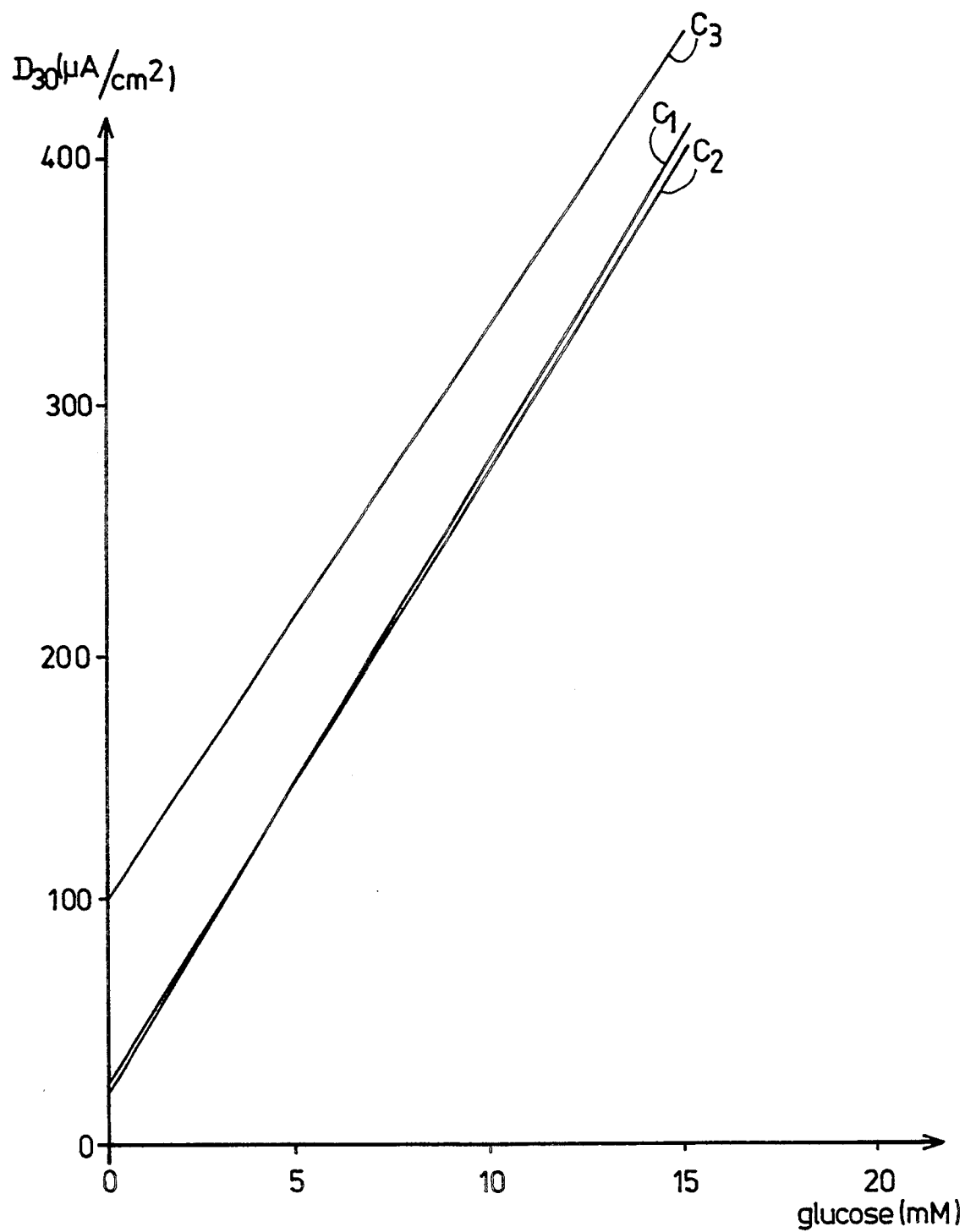

FIG. 16 illustrates the curves obtained. The curves $C_1$, $C_2$ and $C_3$ correspond respectively to the concentrations 0, 100 and 1000 $\mu$M of ascorbic acid per ml blood.

The value of 100 $\mu$M (curve $C_2$) corresponds to the values found in a patient absorbing a normal dose of vitamin C, whereas the value of 1000 $\mu$M (curve $C_3$) corresponds to an excess of ascorbic acid.

It was thus found that when ascorbic acid is present in excess (curve $C_3$), all the glucose concentration values are higher than normal. In contrast, curve $C_2$ is substantially identical to $C_1$ and to the physiological values and it is noted that the presence of ascorbic acid did not affect the results supplied by the sensor.

Acetylsalicylic acid

It was not considered necessary to present a figure illustrating the results obtained because it was found that an amount of acetylsalicylic acid of up to 25 mM yielded straight lines that were substantially identical to those corresponding to an amount of 0 mM of acetylsalicylic acid. It is therefore deduced that the presence of acetylsalicylic acid does not affect the results supplied by the sensor.

What is claimed is:

1. A sensor to be connected to a device for processing an electric signal provided by the sensor and representative of an amount of a component to be measured in a solution, said sensor comprising at least one measuring electrode and one reference electrode insulated from one another, said electrodes defining an area to receive said solution and comprising respective areas defining electrical contacts to be connected to the device for processing the signal, said measuring electrode comprising at least one current collector electrically connected to one of the electrical contacts and coated with a mixture comprising glucose oxidase as an oxidation-reduction enzyme specific to said component and at least one mediator means for transferring electrons between said enzyme and said current collector, and said mediator means comprising tris(4,4'-dimethoxy-2,2'-bipyridine) osmium or bis(4,4'-dimethoxy-2,2'-bipyridine)mono(4,4'-dimethyl-2,2'-bipyridine) osmium.

2. A sensor according to claim 1 wherein the mixture of the measuring electrode further comprises an active conducting material and the mediator means transfers electrons between the enzyme and said active conducting material.

3. A sensor according to claim 2 wherein the active conducting material comprises a conducting polymer.

4. A sensor according to claim 1 wherein the mixture of the measuring electrode comprises an additive forming an immobilization network of at least one of the enzyme of the mixture and of an active conducting material on the surface of the collector of the measuring electrode.

5. An apparatus comprising a sensor according to claim 1 and said device for processing the signal provided by said sensor, said device comprising at least two areas defining electrical contacts to be connected to at least two electrodes of said sensor, an ammeter and means for displaying the amount of the component measured in the solution.

6. A sensor according to claim 2 wherein the mixture of the measuring electrode comprises an additive forming an immobilization network of at least one of the enzyme and the active conducting material of the mixture on the surface of the collector of the measuring electrode.

7. A sensor according to claim 2 wherein the active conducting material comprises a powder of carbon, and wherein the mixture deposited on the collector of the measuring electrode comprises between 1 and 2000 IU of glucose oxidase per mg of carbon powder and between 1 and 10000 μmol of mediator per mg of carbon powder.

8. A sensor to be connected to a device for processing an electric signal provided by the sensor and representative of an amount of a component to be measured in a solution, said sensor comprising at least one measuring electrode and one reference electrode insulated from one another;

said electrodes defining an area to receive said solution and comprising respective areas defining electrical contacts to be connected to the device for processing the signal;

said measuring electrode comprising at least one current collector electrically connected to one of the electrical contacts and coated with a mixture comprising an active conducting material, glucose oxidase as an oxidation-reduction enzyme specific to said component, at least one mediator means for transferring electrons between said enzyme and said current collector and between said enzyme and said active conducting material, and an additive forming an immobilization network of said mixture;

and said mediator means comprising tris(4,4'-dimethoxy-2,2'-bipyridine) osmium or bis(4,4'-dimethoxy-2,2'- bipyridine)mono(4,4'-dimethyl-2,2'-bipyridine) osmium.

9. A sensor according to claim 8 wherein the active conducting material comprises a powder selected from the group consisting of carbon, gold, platinum, palladium and a conducting metal oxide.

10. A sensor according to claim 8 wherein the additive is selected from the group consisting of bovine serum albumin, glutaraldehyde, carbodiimide and a water-soluble polymer.

11. A sensor according to claim 8 wherein the active conducting material comprises a powder of carbon, and wherein the mixture deposited on the collector of the measuring electrode comprises 1 and 2000 IU of glucose oxidase per mg of carbon powder and between 1 and 10000 μmol of mediator per mg of carbon powder.

12. A sensor according to claim 11 wherein the mixture deposited on the collector of the measuring electrode comprises between 10 and 300 IU of glucose oxidase per mg of carbon powder and between 10 and 300 μmol of mediator per mg of carbon powder.

13. A sensor according to claim 12 wherein the mixture deposited on the collector of the measuring electrode comprises about 100 IU of glucose oxidase per mg of carbon powder and about 50 umol of mediator per mg of carbon powder.

14. A sensor according to claim 9 wherein the active conducting material comprises a powder of carbon, and wherein the mixture deposited on the collector of the measuring electrode comprises between 1 and 2000 IU of glucose oxidase per mg of carbon powder and between 1 and 10000 μmol of mediator per mg of carbon powder.

* * * * *